(12) United States Patent
Grönemeyer et al.

(10) Patent No.: US 8,298,282 B2
(45) Date of Patent: Oct. 30, 2012

(54) MAGNETIC RESONANCE-COMPATIBLE MEDICAL IMPLANT

(76) Inventors: Dietrich H. W. Grönemeyer, Sprockhövel (DE); Martin Busch, Witten (DE)

( * ) Notice: Subject to any disclaimer, the term of this patent is extended or adjusted under 35 U.S.C. 154(b) by 137 days.

(21) Appl. No.: 10/581,876

(22) PCT Filed: Dec. 3, 2004

(86) PCT No.: PCT/EP2004/013786
§ 371 (c)(1), (2), (4) Date: Aug. 3, 2006

(87) PCT Pub. No.: WO2005/053575
PCT Pub. Date: Jun. 16, 2005

(65) Prior Publication Data
US 2007/0168016 A1    Jul. 19, 2007

(30) Foreign Application Priority Data

Dec. 5, 2003 (DE) .................... 103 57 334

(51) Int. Cl.
*A61F 2/82* (2006.01)
(52) U.S. Cl. ...................................... 623/1.44
(58) Field of Classification Search ............ 623/1.44, 623/1.15, 1.32; 600/411
See application file for complete search history.

(56) References Cited

U.S. PATENT DOCUMENTS

| 5,667,523 | A | 9/1997 | Bynon et al. | |
| 5,680,046 | A * | 10/1997 | Frederick et al. | 324/318 |
| 6,231,516 | B1 | 5/2001 | Keilman et al. | |
| 6,280,385 | B1 | 8/2001 | Melzer et al. | |
| 6,767,360 | B1 * | 7/2004 | Alt et al. | 623/1.15 |
| 6,884,407 | B1 * | 4/2005 | Unger | 424/9.52 |
| 2002/0188345 | A1 | 12/2002 | Pacetti | |
| 2004/0158310 | A1 * | 8/2004 | Weber et al. | 623/1.15 |
| 2004/0230290 | A1 * | 11/2004 | Weber et al. | 623/1.15 |
| 2005/0033407 | A1 * | 2/2005 | Weber et al. | 623/1.15 |
| 2006/0116755 | A1 * | 6/2006 | Stinson | 623/1.44 |

FOREIGN PATENT DOCUMENTS

| WO | WO 02/30331 A | 4/2002 |
| WO | WO 03/015662 A | 2/2003 |
| WO | WO 2005/013856 | 2/2005 |

OTHER PUBLICATIONS

International Search Report (in German).
Fritzsche S, Thull 4, Hasse A: "Reduction of NMR image artefacts by using optimal materials as diagnostic aids and implants" Biomedizinische Technik, Bd. 39, Nr. 3, Mar. 1994, pp. 42-46, XP002024164, Berlin.

* cited by examiner

*Primary Examiner* — Christopher Koharski
*Assistant Examiner* — Cheryl Miller
(74) *Attorney, Agent, or Firm* — Collard & Roe, P.C.

(57) ABSTRACT

The invention relates to a medical implant or instrument, particularly a vascular endoprosthesis (stent), comprising a deformable structural part. In order to provide an implant of this type that is magnetic resonance-compatible and can be easily and economically produced, the invention provides that the structural part has a two-layer or multilayer design, whereby layers (2,3) have different electrical and/or magnetic properties. The invention particularly provides that the structural part has a frame structure with openings (5) whereby, in different layers (2,3) of the structural part, the openings (5) are each located at different positions not directly located one above the other.

9 Claims, 2 Drawing Sheets

MAGNETIC RESONANCE-COMPATIBLE MEDICAL IMPLANT

CROSS REFERENCE TO RELATED APPLICATIONS

Figure 1:
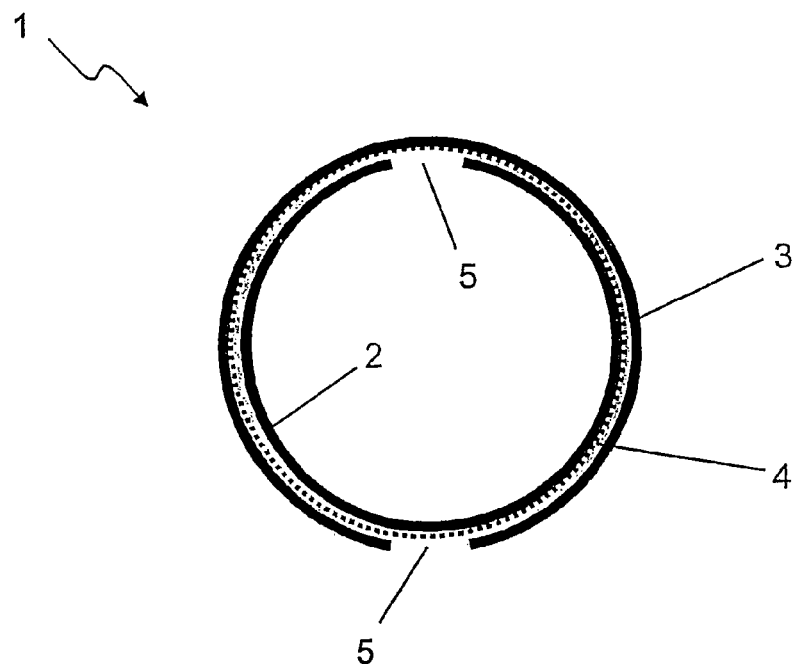

Applicants claim priority under 35 U.S.C. §119 of German Application No. 103 57 334.8 filed Dec. 5, 2003. Applicants also claim priority under 35 U.S.C. §365 of PCT/EP2004/013786 filed Dec. 3, 2004. The international application under PCT article 21(2) was not published in English.

The invention relates to a medical implant or instrument, particularly a vascular endoprosthesis, having a deformable structural part. Furthermore, the invention relates to an MR imaging method for producing an image of a patient situated in the examination volume of an MR device, who has such a medical implant.

Vascular endoprostheses (so-called "stents") and other medical implants or instruments that have a deformable structural part, such as intravascular filter systems, for example, are known from the state of the art. In the case of stents, the structural part is usually formed by metal filaments arranged in grid shape, which are used to support and/or smooth out a damaged coronary blood vessel wall. A stent is positioned in the region of the damaged site of the blood vessel to be treated by means of a balloon catheter, similar to a PTCA treatment. Stents are mainly used to prevent acute blood vessel closures or reforming of a stenosis after PTCA treatments. So-called stent grafts are used for the treatment of aneurysms.

Diagnostic imaging of regions in the surroundings of a stent or a similar medical implant, using magnetic resonance (MR), often proves to be problematic. This can be attributable, for one thing, to the fact that the structural part of the implant situated in the body of the patient being examined consists of paramagnetic material. Because of the magnetic susceptibility of the implant, the magnetic field is distorted in the surroundings of the implant, which are otherwise diamagnetic, so that artifacts are formed in the images that are taken. These images, which contain artifacts, are then generally not usable for diagnostic purposes. Medical implants and instruments that have a structural part consisting of metallic filaments furthermore have the disadvantage that the grid-like or net-like structure acts as a Faraday cage during the MR imaging, so that the high-frequency fields radiated in during MR imaging do not penetrate into the volume within the implant. Because of this shielding, the interior of a conventional stent often remains invisible during MR imaging, and this is disadvantageous. It is particularly disadvantageous because it prevents an early diagnosis of reformation of stenosis in the interior of a stent.

From US 2002/0188345 A1, an MR-compatible stent is known, whose deformable structural part consists of metal filaments that have interruptions at certain points, so that current paths that are closed in themselves, within the framework structure, are prevented. By preventing eddy currents, the result is therefore achieved that the stent cannot act as a Faraday cage. The high-frequency fields radiated in during the MR imaging therefore cannot induce any eddy currents in the framework structure of the stent, and MR imaging also in the interior of the stent is made possible.

However, it is a disadvantage of the stent previously known from the stated US laying-open document that its production is extremely complicated and expensive. This is because in order for the structural integrity of the stent not to suffer, the interruptions made to prevent eddy currents must be bridged with suitable electrically non-conductive material. Adhesives, plastics, and the like are possibilities for this. Furthermore, in order for the metal filaments provided with interruptions to have sufficient stability under shear stress, the interruptions in the case of the previously known stent must additionally have a special shape, which is described in detail in the said US 2002/0188345 A1. The production of these specially shaped interruptions is particularly complicated and technologically difficult. It is furthermore a disadvantage of the previously known stent that no measures are taken to minimize the susceptibility to artifacts in the images taken by means of MR, as mentioned above.

Proceeding from this, the present invention is based on the task of developing a medical implant or instrument, particularly a stent, further in such a manner that MR imaging of the surroundings of the implant situated in the body of a patient is possible, whereby the implant is supposed to be structured as simply as possible and to be producible at low cost.

This task is accomplished by the invention, proceeding from a medical implant of the type stated initially, in that the structural part is composed of two or multiple layers, whereby the layers have different electrical and/or magnetic properties.

The MR compatibility of the medical implant according to the invention results from its multi-layer structure. Because the individual layers have different electrical and/or magnetic properties, according to the invention, compensation of the properties of the individual layers occurs, to a great extent; without the compensation according to the invention, these properties would have a negative effect when taking MR images.

The multi-layer structure particularly has the advantage of particularly simple and inexpensive producibility of the medical implant according to the invention. The deformable structural part of a stent structured according to the invention can consist, for example, of two tube parts having different diameters, which are disposed coaxially one inside the other. In this connection, each individual tube part, as in the case of conventional stents, can be structured by means of a laser, for example, by cutting a framework structure out of a continuous tube, in such a manner that the two tube parts have the desired different electrical properties. After structuring of the tube parts, these can be disposed one inside the other, and glued together using a suitable adhesive. Just as well, the tube parts can first be disposed one inside the other and glued together, and only afterwards be structured in the manner according to the invention, by means of a laser or otherwise. Different magnetic properties result from a suitable selection of the materials for the two tubes.

Similar as in the case of conventional stents, it is practical if the structural part of the medical implant or instrument according to the invention has an expandable framework structure, formed by a plurality of metallic struts connected with one another. In order for the desired MR compatibility to be guaranteed, the framework structure can have interruptions, for example by cutting through individual struts, in such a manner that closed current paths within individual layers of the structural part are avoided. In this way, eddy currents that occur during MR imaging are effectively prevented, so that the medical implant according to the invention does not shield against the high-frequency fields that are radiated in. In this connection, a particularly practical further development results from the fact that the interruptions in different layers of the structural part are situated at different positions, not directly above one another. Because no interruption is provided in a layer at a position in which an interruption is situated in another layer, the structural integrity of the overall arrangement according to the invention is guaranteed, and this is particularly important in the case of stents, so that they can withstand the radial stresses applied by the blood vessel walls. Clearly lower production effort is required to guarantee sufficient structural integrity, according to the invention, than is the case for a stent structure according to the publication cited above.

A particularly practical embodiment of the medical implant according to the invention results from the fact that the interruptions are disposed in such a manner that a continuous current path that extends from one end region of the structural part to the opposite end region is formed, at least within one layer. This continuous current path can advantageously be formed in helix shape, so that the individual layers have the electrical properties of an inductive resistor, in each instance. It is practical in this connection if the continuous current paths formed within different layers of the structural part are connected with one another, so that the inductive resistors of the individual layers add up to an overall impedance, in suitable manner, as needed. It is particularly advantageous to connect the continuous current paths of the different layers by way of at least one electrical capacitor. Thus, a resonator structure is formed overall, which can be utilized in the MR imaging. For this purpose, the resonance frequency of the structure must be coordinated with the resonance frequency of the MR device. The high-frequency fields radiated in during MR imaging are then not shielded, as is the case in conventional stents, but rather, on the contrary, actually reinforced within the implant. Therefore, MR imaging of the volume within a stent configured according to the invention is possible in particularly good manner. The capacitor required for the effect as a resonator can be formed, in particularly simple manner, by means of electrically conductive regions of the layers of the structural part of the medical implant according to the invention that lie on top of one another. Depending on the application case, the continuous current paths formed within the individual layers can also be connected with one another by way of feed-throughs in the end regions of the structural part. By means of such connections, the desired total impedance of the medical implant can be adjusted in targeted manner. If as great an inductive resistor as possible is aimed at, it is practical if the current paths configured in helix shape have an opposite direction of rotation in the different layers, in such a manner that the inductive resistors of the individual layers connected with one another add up, rather than compensating one another.

An alternative possibility of producing a resonator structure by means of the implant or instrument according to the invention consists of disposing the interruptions in the framework structure in such a manner that two or more essentially helical current path segments are formed within at least two layers of the structural part that lie on top of one another, whereby the current path segments of different layers of the structural part are disposed at least partially covering one another. Accordingly, each individual layer has two or more helix-shaped current path segments that are switched behind one another, each of which contributes to the total inductive resistor of the resonator with its inductive resistor. The helix-shaped current path segments of different layers partially overlap, in this connection, so that capacitors are formed in the overlap regions. In total, this structure is structured in the manner of a so-called split-ring resonator, which is known in the field of high-frequency technology. In this connection, disposing two or more helix-shaped current path segments behind one another, each of which can have several helix coils, has the effect that the overall inductive resistor of the structure is sufficiently great so that the resonance frequency lies in the range of usual MR resonance frequencies of approximately 20 to 400 MHz.

In order to avoid the aforementioned magnetic susceptibility effects in MR imaging when using the medical implant according to the invention, it is particularly practical if at least two layers of the structural part consist of materials having magnetic susceptibilities that are opposite to one another. Accordingly, at least one of the layers should consist of a diamagnetic material, while at least one other layer consists of a ferromagnetic or paramagnetic material. The opposite susceptibilities compensate one another to a great extent, so that the effective overall susceptibility of the implant or the instrument is reduced. Then distortions of the magnetic fields in the surroundings of the implant will only occur to a reduced extent any longer, and corresponding artifacts in the MR images that are taken will occur to a reduced extent.

It is practical that in the case of the medical implant according to the invention, the layers of the structural part that consist of electrically conductive material are separated from one another by layers consisting of electrically insulating material. In this way it is assured, in particular, that the desired different electrical properties of the individual layers can be predetermined in targeted manner. In particular, if interruptions are made in the framework structure, in order to prevent the effect of the structural part of the implant as a Faraday cage, electrical connections between the different layers must be prevented, since otherwise, the interruptions could be bridged and thereby become ineffective.

The medical implant according to the invention can be advantageously used in the case of an MR imaging method, for producing an image of a patient situated in the examination volume of an MR device. A paramagnetic contrast agent can be applied intravenously to the patient during the imaging process, in order to suppress magnetic susceptibility artifacts; the contrast agent is composed in such a manner that the paramagnetic susceptibility of the blood in the surroundings of the medical implant is essentially equal to the paramagnetic susceptibility of the medical implant itself. Accordingly, if the surroundings of the medical implant have essentially the same paramagnetic susceptibility properties as the medical implant itself, no local distortions of the magnetic fields will occur. Accordingly, no artifacts will occur in the MR images that are taken. Suitable paramagnetic contrast agents can contain at least one substance from the group of ferrites. The contrast agent GdDTPA that is generally used nowadays can also be used.

Figure 2:
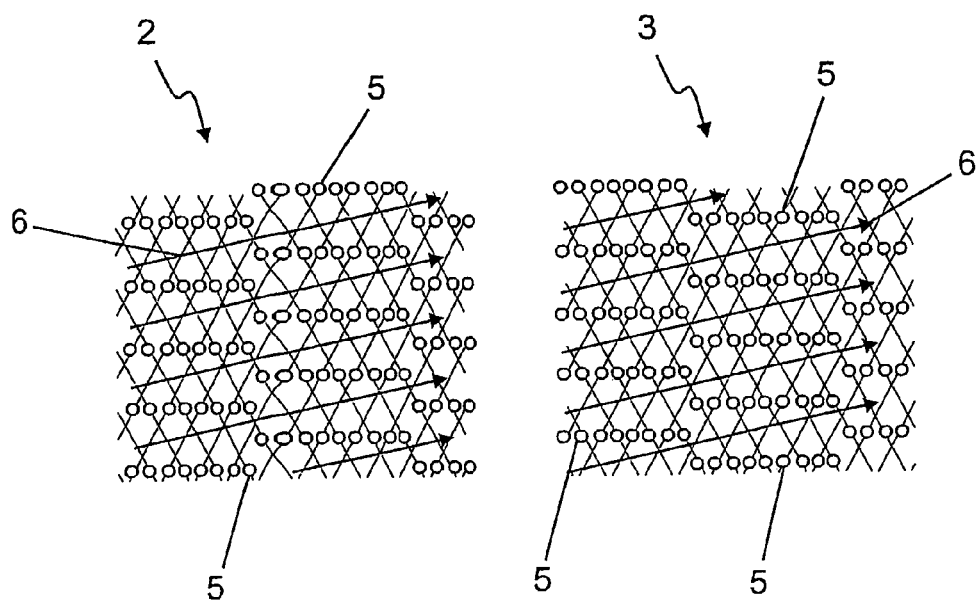
Figure 3:
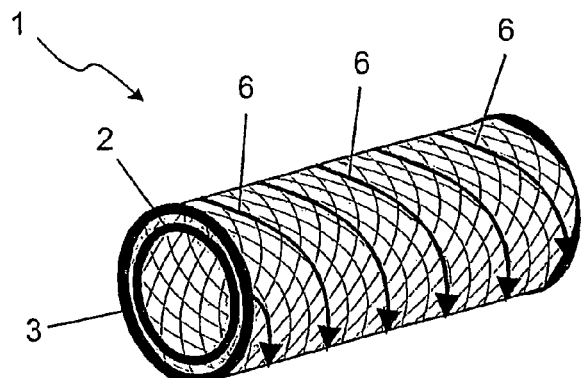
Figure 4:
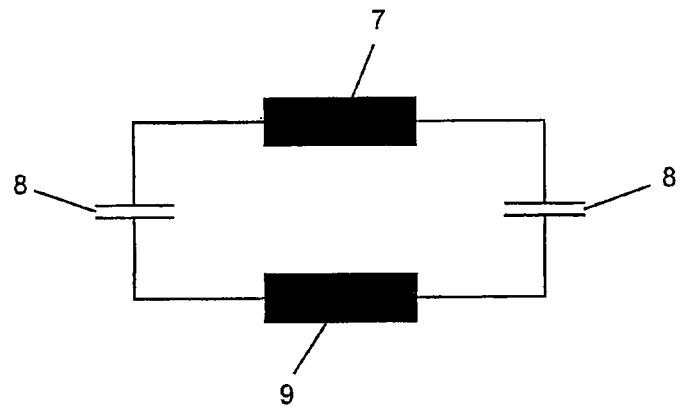
Figure 5:
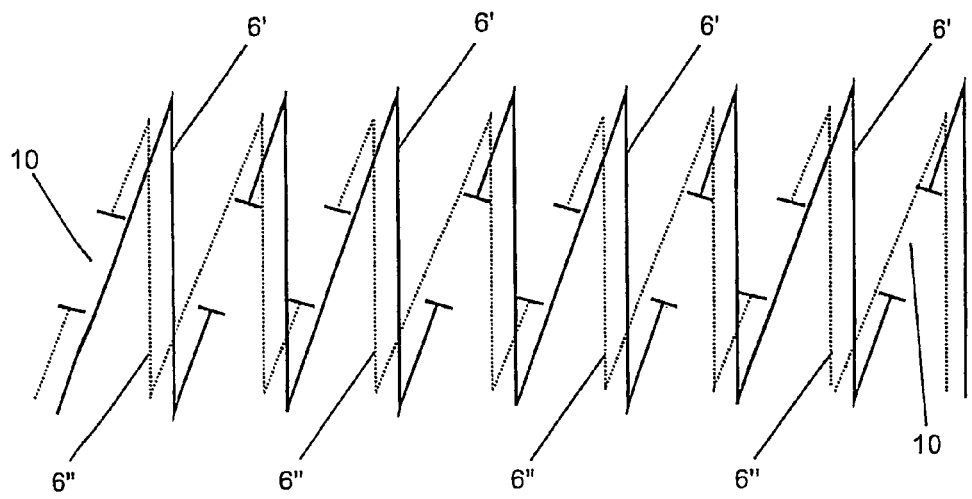

Exemplary embodiments of the invention will be explained in the following, using the figures. These show:

FIG. 1 vascular endoprosthesis according to the invention in cross-section;

FIG. 2 developed view, into the plane of the drawing, of the different structuring of the layers of the implant according to FIG. 1;

FIG. 3 three-dimensional view of the coronary endoprosthesis according to FIG. 1;

FIG. 4 equivalent circuit schematic to illustrate the resonator properties of the implant;

FIG. 5 schematic representation of the split-ring resonator expanded according to the invention.

The medical implant shown in the figures is a stent that is indicated as a whole with the reference number 1 in FIGS. 1 and 3. The stent 1 has a deformable, expandable structural part having a two-layer structure. An inner layer 2 and an outer layer 3 are disposed lying on top of one another. The layers 2 and 3 of the structural part are formed by means of two tube-shaped elements disposed coaxially, which are clearly evident in FIG. 3. The layers 2 and 3, which consist of electrically conductive material, are separated from one another by means of an intermediate layer 4 that consists of electrically insulating material. This can be, for example, a layer of adhesive, by means of which the tube-shaped elements disposed coaxially one inside the other are connected with one another.

In the case of the medical implant shown in the figures, the layers 2 and 3, which form the structural part of the stent, have an expandable framework structure that is formed by a plurality of metallic struts connected with one another. This structure can be seen in FIGS. 2 and 3. The struts are metallic filaments that form a diamond-shaped lattice, overall, in the case of the exemplary embodiment. The framework structure has interruptions 5 that are symbolized by open circles in FIG. 2. FIG. 2 merely shows a detail of the overall structure of the stent. Current paths that are closed in themselves are avoided within the layers 2 and 3 of the structural part, by means of the interruptions 5. Using the developed view, into the plane of the drawing, according to FIG. 2, it is clearly evident that the interruptions 5 are located at different positions, not lying directly on top of one another, in the layers 2 and 3. As a result, it is assured, as explained above, that the structural integrity of the stent 1 as a whole is guaranteed. Furthermore, the interruptions 5 are disposed in such a manner that the tube-shaped layers 2 and 3 have continuous current paths in helix shape, in each instance, as is symbolized by arrows 6 in FIGS. 2 and 3. The helix-shaped current paths 6 form inductive resistors that are connected with one another by way of electrical capacitors. These capacitors are formed by means of the electrically conductive regions of the layers 2, 3 of the structural part that lie on top of one another.

Using the circuit schematic according to FIG. 4, it becomes clear how the inductive resistors and capacitors are connected with one another. An inductive resistor 7 is assigned to the inner layer 2 of the stent 1. By means of the coaxial arrangement of the tube-shaped elements of the stent 1, capacitors 8 are formed, by way of which the inductive resistor 7 of the inner layer 2 is connected with the inductive resistor 9 of the outer layer 3. In total, a resonance circuit is formed in this manner, whereby the capacitor 8 and the inductive resistors 7 and 9 formed by the current paths 6 are coordinated with one another in such a manner that the resonance frequency is equal to the resonance frequency of an MR device, not shown in detail in the figures.

FIG. 5 schematically shows the split-ring structure described above, which can be achieved, according to the invention, by means of suitably arranging the interruptions within the framework structure of the implant. In the representation according to FIG. 5, the solid lines symbolize current path segments 6' within the outer layer 3 of the resonator, while the broken lines represent current path segments 6" that are formed by means of suitably arranging the interruptions within the layer 2. The current path segments 6' and 6" are configured in helix shape, in each instance, and comprise two complete helix coils, in each instance. In the representation of FIG. 5, lines oriented vertically symbolize segments of the helix coils that lie in the back, in a top view of the overall structure, while the slanted lines represent the helix segments that lie in the front. In FIG. 5, it can be seen that four current path segments 6' and 6" are disposed one behind the other in the layers 2 and 3, whereby the individual current path segments are separated from one another by means of insulating segments 10, in each instance. The arrangement is such that an insulating segment 10 of the inner layer 2 is situated approximately in the center region of a current path segment 6' of the outer layer 3. This results in the overall arrangement of the current path segments, which overlap one another at least partially. Thus, an expanded split ring structure is formed, which can be used in the manner described above, as an MR resonator.

The invention claimed is:

1. A medical implant or instrument, having a deformable structural part with an expandable framework structure, formed by a plurality of metallic struts connected with one another, wherein the struts are composed of at least two layers that are glued together, whereby the layers have different electrical and/or magnetic properties, and wherein the struts have interruptions in conductive regions of each of the at least two layers, in such a manner that current paths that are closed in themselves are avoided within each of the at least two layers of the struts, said interruptions being situated in different positions such that interruptions in a first one of the layers do not overlap interruptions in a second one of the layers, wherein the interruptions are disposed in such a manner that a continuous current path of helical shape that extends from one end region of the structural part to the opposite end region is formed, at least within one of said at least two layers.

2. The medical implant or instrument according to claim 1, wherein the interruptions are disposed in such a manner that two or more continuous current paths configured essentially in helix shape are formed within at least two mutually superposed layers of the at least two layers.

3. The medical implant or instrument according to claim 2, wherein the continuous current paths formed within each of the at least two layers of the struts are connected with one another.

4. The medical implant or instrument according to claim 2, wherein the current paths have an opposite direction of rotation in the different layers.

5. The medical implant or instrument according to claim 1, wherein at least two of the at least two layers of the struts comprise materials having opposite magnetic susceptibilities.

6. The medical implant or instrument according to claim 1, wherein the at least two layers of the struts are formed by two or more tube-shaped elements disposed coaxially.

7. The medical implant or instrument according to claim 1, wherein the at least two layers of the struts comprise layers that comprise electrically conductive material separated from one another by intermediate layers comprising electrically insulating material.

8. A medical implant or instrument, having a deformable structural part with an expandable framework structure, formed by a plurality of metallic struts connected with one another, wherein the struts are composed of at least two layers that are glued together, whereby the layers have different electrical and/or magnetic properties, and wherein the struts have interruptions in conductive regions of each of the at least two layers, in such a manner that current paths that are closed in themselves are avoided within each of the at least two layers of the struts, said interruptions being situated in different positions such that interruptions in a first one of the layers do not overlap interruptions in a second one of the layers, wherein the interruptions are disposed in such a manner that two or more continuous current paths configured essentially in helix shape are formed within at least two mutually superposed layers of the at least two layers, wherein the continuous current paths formed within each of the at least two layers of the struts are connected with one another, and wherein the current paths are connected with one another by way of at least one electrical capacitor which is formed by electrically conductive regions of the at least two mutually superposed layers of the struts, wherein the two or more layers of the struts comprise layers that comprise electrically conductive material separated from one another by intermediate layers comprising electrically insulating material.

9. The medical implant or instrument according to claim 8, wherein the capacitor and inductive resistors formed by the current paths are coordinated with one another in such a manner that a high-frequency resonator is formed, a resonance frequency of which is equal to the resonance frequency of an MR device.

* * * * *